United States Patent
Rix

(10) Patent No.: US 12,387,329 B2
(45) Date of Patent: Aug. 12, 2025

(54) METHOD FOR BIOMARKER ESTIMATION

(71) Applicant: Lucida Medical LTD., Cambridge (GB)

(72) Inventor: Antony William Rix, Cambridge (GB)

(73) Assignee: Lucida Medical LTD., Cambridge (GB)

( * ) Notice: Subject to any disclaimer, the term of this patent is extended or adjusted under 35 U.S.C. 154(b) by 384 days.

(21) Appl. No.: 18/245,122

(22) PCT Filed: Sep. 10, 2021

(86) PCT No.: PCT/GB2021/052346
§ 371 (c)(1),
(2) Date: Mar. 13, 2023

(87) PCT Pub. No.: WO2022/053817
PCT Pub. Date: Mar. 17, 2022

(65) Prior Publication Data
US 2023/0252633 A1 Aug. 10, 2023

(30) Foreign Application Priority Data
Sep. 14, 2020 (GB) ..................... 2014432

(51) Int. Cl.
*G06T 7/00* (2017.01)
*G06T 7/11* (2017.01)
*G16H 10/40* (2018.01)

(52) U.S. Cl.
CPC .............. *G06T 7/0012* (2013.01); *G06T 7/11* (2017.01); *G16H 10/40* (2018.01); *G06T 2207/10081* (2013.01); *G06T 2207/10088* (2013.01); *G06T 2207/10104* (2013.01); *G06T 2207/20076* (2013.01); *G06T 2207/20092* (2013.01); *G06T 2207/30081* (2013.01); *G06T 2207/30096* (2013.01)

(58) Field of Classification Search
CPC .......... G06T 7/0012; G06T 7/11; G16H 10/40
USPC ......................................... 382/131
See application file for complete search history.

(56) References Cited

U.S. PATENT DOCUMENTS

| 10,957,041 B2 * | 3/2021 | Yip .................. G06N 3/084 |
| 2020/0258223 A1 | 8/2020 | Yip et al. |
| 2023/0351607 A1 * | 11/2023 | Lu .................. G06T 7/62 |

FOREIGN PATENT DOCUMENTS

| JP | 2017-500537 | 1/2017 |
| WO | WO 2020/144134 | 7/2020 |

OTHER PUBLICATIONS

"IRAC Cancer Today" webpage https://gco.iarc.fr/today/home, 1 page, retrieved on Jun. 28, 2023.
(Continued)

*Primary Examiner* — Allen H Nguyen
(74) *Attorney, Agent, or Firm* — Levine Bagade Han LLP

(57) ABSTRACT

According to the invention there is provided a method of estimating an amount of at least one biomarker for a subject, based on an image of the subject imaged by a medical imaging method, the method comprising: processing the image to identify at least one tissue type within a region of interest of the image and determining an amount of each identified tissue type; associating each identified tissue type with a measure of biomarker production; calculating a total amount of biomarker production for the identified tissue types.

20 Claims, 3 Drawing Sheets

| | | | (393) Low-risk condition | | (394) High-risk condition | |
|---|---|---|---|---|---|---|
| (390) Tissue type | (391) Volume mL | (392) Relative vascularity | (3931) Biomarker density ng/mL/mL | (3932) Biomarker contribution | (3941) Biomarker density ng/mL/mL | (3942) Biomarker contribution |
| (310) Cancer-suspicious | 3.1 | 10.3 | 1.03 | 3.193 | 1.545 | 4.7895 |
| (311) Benign abnormality | 2.5 | 3.2 | 0.256 | 0.64 | 0.256 | 0.64 |
| (300) Residual benign PZ | 5.3 | 1.1 | 0.0132 | 0.06996 | 0.0132 | 0.06996 |
| (301) Residual benign TZ | 19.2 | 1.5 | 0.03 | 0.576 | 0.03 | 0.576 |
| (320) Expected biomarker production given condition, ng/mL | | | | 4.47896 | | 6.07546 |

(56) References Cited

OTHER PUBLICATIONS

"Risk Calculators 1-6, European Randomized Study of Screening for Prostate Cancer (ERSPC)" webpage www.prostatecancer-riskcalculator.com, 2 pages, retrieved on Jun. 28, 2023.
Cao et al., Joint Prostate Cancer Detection and Gleason Score Prediction in mp-MRI via FocalNet, IEEE Transactions on Medical Imaging, 38(11), pp. 2496-2506, 2019.
Gaur et al—Can Computer-Aided Diagnosis Assist in the Identification of Prostate Cancer on Prostate MRI? a multi-center, multi-reader investigation, Oncotarget, 9(73), pp. 33804-33817, 2018.
Isensee et al., Automated Design of Deep Learning Methods for Biomedical Image Segmentation, pp. 1-55, 2020.
Partin et al., Clinical Validation of an Epigenetic Assay to Predict Negative Histopathological Results in Repeat Prostate Biopsies, J Urol., 192(4), pp. 1081-1087, 2014.
Prostate Imaging Reporting and Data System Version 2.1, American College of Radiology, 2019 https://www.acr.org/Clinical-Resources/Reporting-and-Data-Systems.
Schoots et al., Personalizing prostate cancer diagnosis with multivariate risk prediction tools: how should prostate MRI be incorporated? World Journal of Urology, 38, pp. 531-545, 2020.
Schroeder et al., Screening and Prostate-Cancer Mortality in a Randomized European Study, N Engl J Med; 360, pp. 1320-1328, 2009.
Tixier et al—Reliability of Tumor Segmentation in Glioblastoma: Impact on the Robustness of MRI-radiomic Features, Department of Medical Physics, 46(8), pp. 3582-3591, 2019.
Verma et al., European Urology, European Association of Urology, 66, pp. 964-965, 2014.
Westphalen et al., Variability of the Positive Predictive Value of PI-RADS for Prostate MRI across 26 Centers: Experience of the Society of Abdominal Radiology Prostate Cancer Disease-focused Panel, Radiology, 296, pp. 76-84, 2020.
Yang et al., Identification of Low Prostate-Specific Antigen, High Gleason Prostate Cancer as a Unique Hormone-Resistant Entity with Poor Survival: A Contemporary Analysis of 640,000 Patients, Journal of Clinical Oncology, 99, pp. 285-287, 2017.

* cited by examiner

Figure 3

|  |  |  | (393) Low-risk condition | | (394) High-risk condition | |
|---|---|---|---|---|---|---|
| (390) Tissue type | (391) Volume mL | (392) Relative vascularity | (3931) Biomarker density ng/mL/mL | (3932) Biomarker contribution | (3941) Biomarker density ng/mL/mL | (3942) Biomarker contribution |
| (310) Cancer-suspicious | 3.1 | 10.3 | 1.03 | 3.193 | 1.545 | 4.7895 |
| (311) Benign abnormality | 2.5 | 3.2 | 0.256 | 0.64 | 0.256 | 0.64 |
| (300) Residual benign PZ | 5.3 | 1.1 | 0.0132 | 0.06996 | 0.0132 | 0.06996 |
| (301) Residual benign TZ | 19.2 | 1.5 | 0.03 | 0.576 | 0.03 | 0.576 |
|  |  |  |  |  |  |  |
| (320) Expected biomarker production given condition, ng/mL |  |  |  | 4.47896 |  | 6.07546 |

METHOD FOR BIOMARKER ESTIMATION

This application is a U.S. national phase application of International Application No. PCT/GB2021/052346 filed on Sep. 10, 2021, which claims the benefit of priority to GB 2014432.5, filed on Sep. 14, 2020, the contents of which are incorporated herein by reference in their entireties.

BACKGROUND ART

Prostate cancer is the most common cancer in men in many countries, with 1.3 million new diagnoses per year worldwide [1]. Previous screening methods, in particular the prostate specific antigen (PSA) test, have been controversial due to concerns with overdiagnosis, and this has recently led to recommendations for prostate magnetic resonance imaging (MRI) examinations prior to biopsy. PSA is attractive as it is low cost and requires only a blood sample to test.

A particular problem occurs for men with high PSA levels but low clinical risk of cancer, for example those with negative MRI examinations, suspected prostatitis, known insignificant cancer, or negative biopsy results. These men will naturally be worried, and may excessively seek medical attention, leading to costs and undue and potentially harmful treatments.

A related problem also occurs for men with low PSA levels but potentially clinically significant cancer. Current MRI and biopsy methods are not guaranteed to identify cancer, especially when it is small or the proportion of cancerous cells is low. In these cases, clinicians and the patients may be falsely reassured that a low PSA level is safe, delaying diagnosis and treatment for what could then become harmful disease.

Recently, artificial intelligence methods, in particular those based on machine learning, have been proposed as an aid to the process of MRI interpretation. Along with statistically derived risk calculators that have also been proposed, these methods offer promise to help make prostate MRI analysis faster or more accurate.

However, none of these described methods adequately addresses the problems described above, and there remains a need to account for the limitations in the PSA test.

The prostate specific antigen (PSA) blood test has been used for initial screening and has potential to detect the disease early in some cases, reducing complications and deaths [2]. More recently, PSA has been combined with other clinical information, for example urinary tract symptoms, family history of cancer, digital rectal examination, and prostate volume [3]. By combining information, this has the potential to make more accurate predictions of risk. PSA density, which is calculated by dividing the PSA level by the estimated gland volume, has also been found to provide a useful improvement in prostate cancer risk identification, compared to raw PSA values, as it can reduce or eliminate variation in PSA level due to absolute gland volume [4]. Radiologists may consider a threshold PSA density, for example 0.1 ng/mL/mL, as part of their analysis.

The state-of-the-art today is represented by [5][6], which are hereby incorporated by reference, which describe a range of approaches to identifying patients at risk of prostate cancer. By combining PSA density and other clinical indications with MRI scores according to the PI-RADS 2.1 or similar classification scheme, these are able to obtain an accurate prediction about whether a patient has clinically significant prostate cancer. In future, risk indicators derived from AI or radiomics methods will be able to be used instead of or alongside the MRI scores in such calculations.

PSA density is often a significant factor in such tests, and this introduces a significant weakness. Yang et al found that 5.6% of significant prostate cancers were diagnosed at PSA levels<=2.5 ng/mL, where PSA density will also be very low (in most cases, well below 0.1 ng/mL/mL) [8].

A number of other tests have been proposed as alternatives or additions to PSA, including free PSA and SelectMDx [9], and these may also include or be used with risk calculation methods similar to those described above.

It will be appreciated that the methods used in PI-RADS and prostate MRI are also applicable, with the necessary changes, to imaging many other types of cancer, for example in whole-body diffusion weighted imaging (WB-DWI or WB-MRI), breast cancer MET-RADS-P and similar. While this specification uses prostate cancer as an example, the methods may be applied to imaging for other cancers without loss of generality.

Similarly, alternatives to PSA already exist for certain other types of cancer. The field of liquid biopsy is developing methods that will identify the presence of further types of biomarker that is potentially indicative of cancer.

Analysis of MRI prior to biopsy, for example according to the PI-RADS 2.1 methodology [6], has been shown in studies to help identify patients with clinically significant prostate cancer [7]. However, it is also not a perfect test, with a positive predictive value (PPV) as low as 35% [7], and in present clinical practice is often used alongside PSA density for selecting patients for biopsy.

Methods applying machine learning (ML) techniques to medical imaging of cancer are also now being developed, building on MRI imaging techniques such as those described in the citations, as well as CT, X-ray mammography and other imaging methods. It is known that ML, together with related deep learning and image processing methods such as atlas-based segmentation, now provides efficient methods for segmenting organs of interest in medical images [10]. Related ML methods, including methods based on radiomic features, have also been applied with some success to the task of segmenting tumours in medical images [11][12].

Where such ML methods have been applied in cancer imaging, researchers have focused on providing information such as heatmaps for analysis by radiologists (computer aided diagnostics, image fusion), segmentations of organs or tumours to support biopsy, radiotherapy or analysis of tumour progression, and in risk calculations such as identifying patients for biopsy or evaluating prognosis. Systems using these methods have shown promising performance when compared to manual methods such as PI-RADS. As with manual evaluation, performance of such systems, in particular of risk calculators, may be enhanced by introducing information from biomarkers such as PSA or PSA density, as well as scores from radiological or clinical evaluation.

Nevertheless, for many cancers, the methods outlined above do not provide a solution with perfect sensitivity or selectivity, and thus the problems described above remain. Restated, we do not have a satisfactory solution to explain a high biomarker result, even when other tests are negative; and conversely, we know that there is a subset of cases where low biomarker results might incorrectly be presumed to be negative.

SUMMARY OF THE INVENTION

The invention described herein overcomes such limitations by providing embodiments that are able to account for a biomarker test result, such as PSA, by reference to medical imaging, available clinical and patient data, and histopathology findings.

Advantageously, this allows a patient and clinicians to be provided with a measure, or a range of measures, of the biomarker that would be expected given the known findings. For a patient with benign findings but a high biomarker level, this can help avoid further clinical interventions that may be unnecessary and harmful. For a patient with possible significant cancer but a low biomarker level, this can help avoid false reassurance and ensure that appropriate clinical tests are made to achieve the correct diagnosis and treatment.

According to an aspect of the invention, there is provided a method of estimating an amount of at least one biomarker for a subject, based on an image of the subject imaged by a medical imaging method, the method comprising: processing the image to identify at least one tissue type within a region of interest of the image and determining an amount of each identified tissue type; associating each identified tissue type with a measure of biomarker production; calculating a total amount of biomarker production for the identified tissue types.

Optionally, wherein at least one of the at least one tissue types is an abnormal tissue type. Optionally, wherein the abnormal tissue type is associated with the production of the at least one biomarker at a level higher by a predetermined amount, or lower by a predetermined amount, than a normal level associated with a normal tissue type. Optionally, wherein the abnormal tissue type is tumour tissue and/or cancer tissue.

Optionally, wherein at least two tissue types are identified. Optionally, wherein at least one of the at least two tissue types is a normal tissue type. Optionally wherein the normal tissue type is associated with the production of the at least one biomarker at a normal level. Optionally, the normal level is zero.

Optionally, the processing of the image comprises identifying a most probable type of tissue present at a region of the image within the region of interest from a plurality of possible tissue types.

Optionally, the processing of the image comprises identifying a plurality of possible tissue types present at a region of the image within the region of interest and a respective probability of the region the image corresponding to each possible tissue type, and the calculation of total biomarker production includes weighting a measure of biomarker production associated with each possible tissue type by their respective probability.

Optionally, the probability of a region the image corresponding to a particular tissue type is determined based on characteristics of the image data. Optionally, the probability of a region the image corresponding to a particular tissue type is determined, at least in part, based on relevant clinical data about the subject. Optionally, the relevant clinical data comprise one or more of: age, actual biomarker level, previous biomarker level, digital rectal examination result, indicator of known or suspected inflammation, indicator of known or suspected infection, family history of related cancer types, histopathology results obtained from tissues associated with suspected cancer, genetic tests associated with a suspected cancer, family history or ethnic group membership associated with increased or decreased risk of cancer or biomarker production.

Optionally, the identified tissue types are adjusted based on data input by a human.

Optionally, each identified tissue type is associated with a measure of biomarker production based on a database of biomarker production for possible tissue types.

Optionally, the measure of biomarker production associated with a tissue type is based, at least in part, on subject-specific characteristics. Optionally, the characteristics include at least one of: a measure of the subject's tissue metabolism, a measure of the subject's heart rate.

Optionally, a plurality of different tissue types with relative probabilities are identified for a region of the image, and the total amount of biomarker production comprises an expected range within a predetermined confidence interval.

Optionally, the medical imaging method comprises one of: MRI, CT, PSMA PET CT, choline PET CT.

Optionally, the biomarker comprises one of: PSA, Immunoglobulin, CA 125, calcitonin, AFP, HCG, circulating tumour cells, circulating tumour DNA.

Optionally, the biomarker is PSA, the imaging method is MM, and the region of interest comprises the subject's prostate.

Optionally, the method further comprises determining a variance for biomarker production by means of one or more of the following:
(i) associating a biomarker density variance with at least one tissue type
(ii) determining a variance of a volume estimate of at least one tissue type
(iii) determining a plurality of biomarker production levels corresponding to a plurality of different possible identified tissue types for a region of the image, different scenarios and/or different conditions.

According to a second aspect of the invention there is provided a method of estimating biomarker production of a particular tissue type, the method comprising: processing images of a plurality of test subjects with known biomarker levels imaged with a medical imaging method to identify one or more tissue types within a region of interest; determining, by a machine learning method, a relationship between the amount of each tissue type and the known biomarker level; calculating an estimated biomarker production for a predetermined amount of each tissue type.

Optionally, the method of the second aspect comprises determining a variance for the estimated biomarker production, by: calculating an estimated total amount of biomarker for an image of a test subject based on the estimated biomarker production; and comparing the estimated total amount of biomarker with an actual amount of biomarker for the test subject.

According to a third aspect of the invention there is provided a computer program product configured to perform the steps of the method according to the first aspect, when executed on a computer.

According to a fourth aspect of the invention there is provided a computer program product configured to perform the steps of the method according to the second aspect, when executed on a computer.

BRIEF DESCRIPTION OF THE DRAWINGS

The invention may be realised in the embodiments and variations described below. References to numbers in round brackets refer to the provided figures.

The embodiments as a whole are represented by the schematic shown in FIG. 1.

Figure 1:
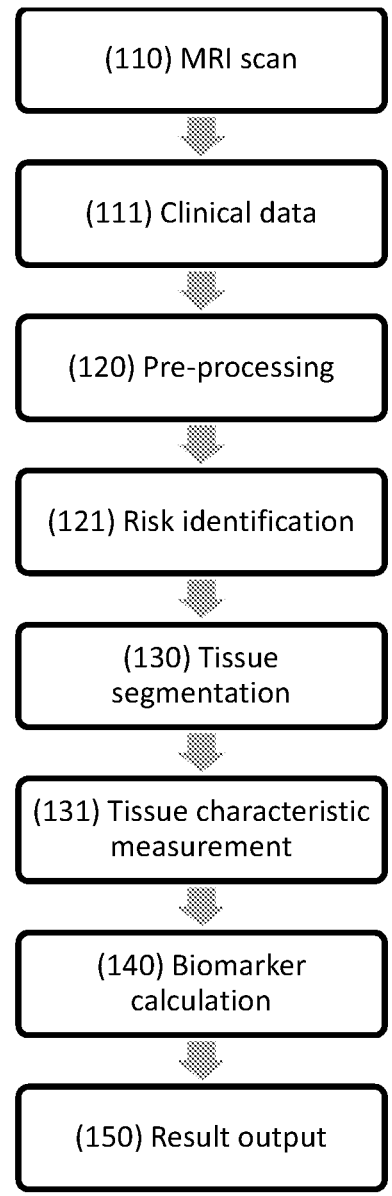
Figure 2:
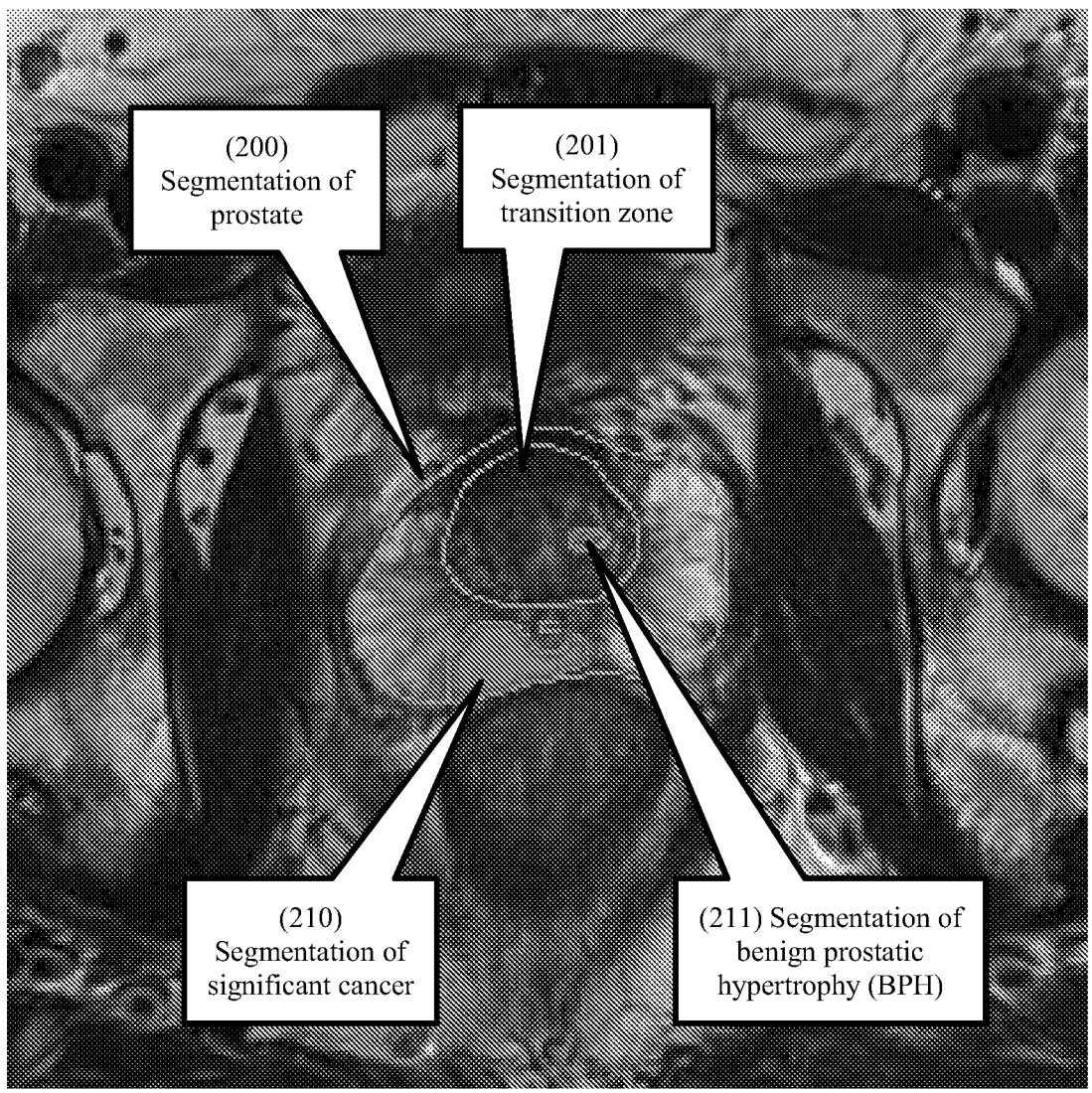

An illustration of the results of a segmentation method is shown in FIG. 2.

FIG. 3 is a table of values based on the segmentation of FIG. 2, for calculating an expected biomarker level.

DETAILED DESCRIPTION

A patient is imaged with a medical imaging device (110) that provides an image or images of a region of interest in at least two dimensions. Preferably, the medical imaging device is an MRI scanner and the images comprise multiparametric imaging of the prostate captured in compliance with the imaging specifications in the PI-RADS protocol [6].

Preferably, the patient's relevant clinical data (111) is also provided, comprising any of the following: age, actual PSA level, previous PSA level, digital rectal examination result, indicator of known or suspected inflammation, indicator of known or suspected infection, family history of related cancer types, histopathology results obtained from tissues associated with suspected cancer, genetic tests associated with a suspected cancer, family history or ethnic group membership associated with increased or decreased risk of cancer or biomarker production.

In a preferred embodiment, the image or images are processed by at least one segmentation method (130) to determine an approximate segmentation of tissues observed in the scan, characterised in that the segmentation method shall identify at least one region of at least one benign tissue type and, where the segmentation method determines a risk of cancer, the segmentation method shall identify at least one region of at least one abnormal tissue type.

Beneficially, the at least one benign tissue types identified by the at least one segmentation method shall represent at least one tissue that may be present and that is associated with the production of at least one biomarker. Preferably, the benign tissue types shall comprise the whole prostate or the zones of the prostate described in the PI-RADS protocol [6], including at least the transition zone and peripheral zone. Preferably, the biomarker shall be PSA.

Beneficially, the at least one abnormal tissue types identified by the segmentation method shall represent at least one tissue that may be present and that produces the at least one biomarker at a level that is at least 25% higher or lower per unit volume than at least one benign tissue type. Preferably, the abnormal tissue types shall comprise at least one of the following: benign prostate hypertrophy (BPH), inflammation, granulomatous prostatitis, atypical acini, calcification, Gleason pattern 3, Gleason pattern 4, Gleason pattern 5, adenocarcinoma, sarcoma, cribiform pattern.

A segmentation method may be a deep learning segmentation model, U-net, V-net, radiomic method, or any of the segmentation or tumour identification methods described in [10][11][12][13], characterised in that the segmentation method is adapted to identify a most likely type of tissue present at a voxel or segmentation region. The segmentation method may operate in a plurality of stages.

Beneficially, pre-processing methods (120) known in the art of medical image analysis may be applied prior to segmentation to facilitate the segmentation method.

Beneficially, the segmentation method may be preceded by a method of risk identification (121) that determines at least one risk of cancer being present, according to the method described in [5]. Beneficially, the segmentation method may be adapted to incorporate the at least one risk in its determination of the relative likelihood that cancer tissue types are present and identification of regions of abnormal tissue type.

In the preferred embodiment, the segmentation method identifies only the regions associated with the production of the biomarker and identifies at least three tissue types, namely at least one organ associated with biomarker production, regions of benign hypertrophy or atrophy associated with the biomarker, and regions of biomarker-producing cancer.

The identified regions may or may not be restricted to the at least one organ, where related cancer or biomarker production may or may not be restricted to the at least one organ.

Beneficially, the segmentation method is also able to identify regions of non-biomarker-producing cancer, as a distinct type from benign tissues and biomarker-producing cancer. In the preferred embodiment, the segmentation method does not identify tissues outside the organ associated with the biomarker.

The term organ is used without limitation and may apply to multiple similar organs, for example the two kidneys, groups of similar structures such as bone, or related body systems such as the lymphatic system.

In a preferred embodiment, each tissue type output by the segmentation method is associated with a measure of biomarker production, such as a biomarker density, and the segmentation method enables each voxel of a 3D image (or pixel for a 2D image) that falls within the determined segmentations to be associated with at least one tissue type, or to be determined that no relevant tissue type is present at that location. For each location in the segmentations, the biomarker calculation method (140) retrieves the applicable measure of biomarker production or biomarker density, and sums these measures (accounting for the relative volume of each voxel or pixel) to determine at least one overall biomarker level indicative of the biomarker production of the imaged tissues.

The at least one overall biomarker level is output as a result (150) and may be used for clinical interpretation or subsequent tests. The clinical history data may also be output. The at least one overall biomarker level may be used in place of or in addition to a physical biomarker test result for any of the following purposes: confirming a physical biomarker test result; identifying patients who may avoid biopsy; determining the need to biopsy; identifying disease progression; identifying treatment response; selecting treatment; calculating a risk of cancer; calculating a prognosis.

The terms "associated with the production of a biomarker", "produces a biomarker" and "does not produce" are used herein without limitation and include tissues that may induce or lead to the production of a biomarker, for example through inflammatory or immune system responses or by breakdown of a chemical or protein, as well as or instead of the direct production of the biomarker.

In the case of normal tissues or tissues of relevant types, a tissue type may not lead to the production of the biomarker and this may be represented by a measure of biomarker production substantially equivalent to zero, or by omitting such tissues from the segmentations.

In a preferred embodiment, the segmentation method may identify a plurality of tissue types each with at least one measure of relative likelihood that that tissue type is present in the respective location or region. Further, each tissue type shall preferably be associated with both an expected value and range or variance of the biomarker density in such tissue type. According to this embodiment, an expected value of a biomarker is calculated in the biomarker calculation method (140) by weighting a biomarker density of each tissue type according to its relative likelihood. Further, in this embodiment, a likely range of measures of a biomarker may be calculated in the biomarker calculation method (140) by determining a measure of the variance of the biomarker density at each voxel according to the relative likelihoods, expected values and variances of the tissue types, and aggregating such measures of variance for the patient as a whole to derive a variance, standard deviation or confidence interval range according to well-known statistical methods, thereby permitting an expected range of the biomarker to be determined given the observed images and output as part of the result (150).

A person skilled in the art of modelling statistical uncertainty will appreciate that alternative methods may also be used to determine a range or variance of a biomarker, including without limitation Bayesian methods, Gaussian processes, Monte-Carlo simulation, random forests, and decision trees.

A preferred embodiment addresses uncertainty in whether cancer is present or not by providing, for patients with possible cancer, at least two values or ranges of a biomarker, each value or range representing an estimated value of the biomarker on the assumption that at least one abnormal tissue type identified by the segmentation model is present or absent. In this embodiment, this is achieved in the biomarker calculation method (140) by performing the calculation on the assumption that the at least one abnormal tissue type is present with 100% likelihood, and repeating the calculation on the assumption that the at least one abnormal tissue type is absent and that the region is represented by an alternative benign or alternative benign tissue type.

A particular benefit of the invention is its ability to account for patient-specific tissue characteristics (131), namely variations in the biomarker density that arise as a result of differences in the metabolic rate of the patient and variations in the vascularity and inflammation associated with the biomarker-producing tissues. In a preferred embodiment, at least one measure of tissue metabolism is determined in relation to the rate of uptake of contrast agent in contrast-enhanced imaging. In an alternative embodiment, at least one measure of tissue metabolism is determined by identifying areas of suspected inflammation with a segmentation method, and assigning a value representing increased tissue metabolism to such areas of suspected inflammation. In a further alternative embodiment, at least one measure of patient heart rate is determined with reference to clinical data, and an increasing value of tissue metabolism is assigned in accordance with at least one of the following: in proportion to, or through an increasing function of, heart rate; as a result of receiving an indication from the patient's clinical history of recent suspected inflammation; in relation to the patient's age. In this preferred embodiment, at least one tissue type is assigned an increased value of an expected biomarker density or measure of the variance of the biomarker density in relation to an increased value of tissue metabolism.

Biopsy and histopathology analysis is often available for certain tissues of interest as part of the process of diagnosing or managing cancer, and the presence of cancer in such analysis provides a positive diagnosis with high confidence. In a preferred embodiment, the clinical data input (111) permits the entry of at least one histopathology finding indicating that a particular tissue type is present at a location. An annotation segmentation may be provided indicating the expected extent of such tissue type. In this embodiment, tissues in proximity to such at least one histopathology finding are assigned to the indicated tissue type.

In an alternative embodiment, candidate tissue segmentations may be made available to a human operator for review and possible correction subsequent to step (130), and such reviewed and corrected segmentations shall be used in the remainder of the calculation.

It will be understood by one skilled in the art that while the proposed embodiments are described with respect to prostate multiparametric MRI of the prostate organ and the PSA test, they may be applied with the necessary changes to several clinical indications, imaging of other regions of the body, other imaging methods including alternative MRI protocols, CT, PSMA PET CT, choline PET CT, and other biomarker tests, including without limitation immunoglobulin testing for multiple myeloma, CA 125 for ovarian cancer, calcitonin for medullary thyroid cancer, AFP for liver cancer, HCG for certain germ cell tumours, circulating tumour cell tests, and circulating tumour DNA tests for cancer.

It will be understood from the complexity of the embodiments and their reliance upon automated analysis of physically obtained medical images or histopathology results, that this invention is no simple mental act and is not excluded matter. The embodiments combine available information of many types in a way that could not reliably be calculated mentally or by hand. The embodiments depend on and extend known methods for medical imaging and histopathology, and provide a result equivalent to a physical test. We therefore submit that the proposed embodiments are patentable.

It remains to consider how the segmentation method and biomarker density and variance values may be determined for use in the proposed embodiments.

A segmentation method may be implementing using a plurality of deep learning or machine learning segmentation models, as described in any of references [10][11][12][13], trained and validated using expert human annotations of the respective tissue types in a selection of patient cases according to training and validation methods known in the art of machine learning. A segmentation method may alternatively or additionally involve the direct input of human annotations, or human correction of machine-generated segmentations.

A database of biomarker densities for the respective tissue types may be determined by the following biomarker density training process. A number of patient cases with known clinical history, measured biomarker level, and medical imaging are assembled into a dataset and a table is created with one row for each patient case and one column for each known measurement or data point. A segmentation model is applied to calculate the volume of each tissue type for each patient case and this is recorded in the table. A machine learning method such is then applied to determine a relationship between the volume of each tissue type and the target measured biomarker level. Where the machine learning method is least squares linear regression, the method may be arranged such that the regression weight applied to each tissue type represents the expected biomarker density value of such tissue type. Alternatively or subsequently, values of biomarker density may be manually adjusted with reference to a plurality of examples to determine a set of values for clinical use.

A database of values of biomarker variance may be established as follows. A dataset is assembled as described for the biomarker density training process described in this specification. The biomarker density training process is applied to determine an expected biomarker level for each patient in the dataset. A standard error is calculated for each patient by subtracting the actual measured biomarker level from the expected biomarker level, and this is squared to produce a squared error estimate. The biomarker density training process is then applied, except that in this case, the target for regression is the squared error estimate, and the weights determined in regression represent the expected biomarker density variance. This set of parameters may then be applied to the respective embodiment of the biomarker calculation method (140) described above.

The operation of the segmentation method (130) according to an implementation of a preferred embodiment is illustrated in FIG. 2, where:
- (200) represents the segmentation of the prostate organ as a whole, and is the default segmentation unless another more specific tissue type is identified; the dominant tissue type in this outer region predominantly comprises the peripheral zone of the prostate
- (201) represents the segmentation of the transition zone of the prostate
- (210) represents the segmentation of significant (Gleason 3+4 or higher) grade prostate cancer
- (211) represents the segmentation of a small nodule of benign prostatic hypertrophy (BPH).

In this embodiment, the segmentations are exclusive, that is, any voxel is associated with only one tissue type or is not of interest for the analysis.

Each of the regions identified in the segmentation are associated with the production of PSA at different rates. An overall estimated measure of PSA is determined by calculating the volume of each segmented tissue type, multiplying the volume of each segmented tissue type by the expected PSA density of the respective tissue type, and summing the results.

By way of illustration, a preferred embodiment is demonstrated by the calculation shown in FIG. 3, which extends the example of FIG. 2, wherein:
- (390) denotes that the cells below relate to tissue types identified through segmentation
- (300) represents the tissue type corresponding to benign peripheral zone
- (301) represents the tissue type corresponding to benign transition zone
- (310) represents the tissue type corresponding to a region suspicious of cancer
- (311) represents the tissue type corresponding to a benign abnormality such as benign prostatic hypertrophy tissues outside of the denoted segmentations are assumed not to contribute to production of the relevant biomarker
- (391) gives the volume of the respective tissue type determined through segmentation
- (392) gives an estimate of relative vascularity, a patient-specific characteristic determined by reference to the dynamic contrast-enhanced sequences of medical imaging, patient metabolic rate and/or patient heart rate
- (393) denotes the expected biomarker levels if the suspicious region represents a low-risk condition, in this example prostatitis or Gleason 3+3
- (3931) gives the relative biomarker production density expected for the given tissue type taking into account the patient-specific characteristic (392), for this low-risk condition
- (3932) determines the contribution of the volume of the tissue type to biomarker production, by multiplying the volume (391) by the biomarker production level (3931), for this low-risk condition
- (394) denotes the expected biomarker levels if the suspicious region represents a high-risk condition, in this example Gleason 3+4
- (3941) gives the relative biomarker production density expected for the given tissue type taking into account the patient-specific characteristic (392), for this high-risk condition
- (3942) determines the contribution of the volume of the tissue type to biomarker production, by multiplying the volume (391) by the biomarker production level (3941), for this high-risk condition
- (320) denotes the biomarker production that would be expected to be measured, by summing the values above in column (3932) and (3942), indicating that if the condition is low-risk, a value of approximately 4.48 ng/mL would be expected, and that if the condition is high-risk, a value of approximately 6.08 ng/mL would be expected.

With reference to the findings illustrated in FIG. 3, an actual biomarker test result (for example, a PSA test result) of 4.5 ng/mL or lower might be considered to be low risk, while an actual biomarker test result of 6.0 ng/mL or higher might be considered to be high risk.

REFERENCES

[1] IARC Cancer Today, 2020, https://gco.iarc.fr/today/
[2] Screening and Prostate-Cancer Mortality in a Randomized European Study, Fritz H. Schroeder et al, N Engl J Med 2009; 360:1320-1328 https://www.nejm.org/doi/full/10.1056/NEJMoa0810084
[3] Risk Calculators 1-6, European Randomized Study of Screening for Prostate Cancer (ERSPC), 2019, https://www.prostatecancer-riskcalculator.com/
[4] PSA density improves prediction of prostate cancer, Ashok Verma et al. Can J Urol. 2014 June; 21(3) 7312-21. https://pubmed.ncbi.nlm.nih.gov/24978363/
[5] Personalizing prostate cancer diagnosis with multivariate risk prediction tools: how should prostate MRI be incorporated?, Ivo G. Schoots and Anwar R. Padhani, World Journal of Urology (2020) 38:531-545, https://doi.org/10.1007/s00345-019-02899-0
[6] Prostate Imaging Reporting and Data System Version 2.1, American College of Radiology, 2019 https://www.acr.org/Clinical-Resources/Reporting-and-Data-Systems/PI-RADS
[7] Variability of the Positive Predictive Value of PI-RADS for Prostate MRI across 26 Centers, Westphalen A C et al, Radiology 2020; 00:1-10 https://doi.org/10.1148/radiol.2020190646
[8] Identification of low prostate-specific antigen, high Gleason prostate cancer as a unique hormone-resistant entity with poor survival: A contemporary analysis of 640,000 patients, Yang D D et al, Journal of Clinical Oncology 35, no. 15_suppl (May 20, 2017) 5080-5080. DOI: https://doi.org/10.1200/JCO.2017.35.15_suppl.5080
[9] Clinical validation of an epigenetic assay to predict negative histopathological results in repeat prostate biopsies, Partin A W et al, J Urol. 2014 October; 192(4):1081-7. https://doi.org/10.1016/j.juro.2014.04.013
[10] Isensee, F et al. Automated design of deep learning methods for biomedical image segmentation. arXiv: 1904.08128v2 [cs.CV] 2 Apr. 2020 https://arxiv.org/pdf/1904.08128.pdf
[11] Cao, R et al. Joint Prostate Cancer Detection and Gleason Score Prediction in mp-MRI via FocalNet, IEEE Transactions on Medical Imaging, vol. 38, no. 11, pp. 2496-2506, November 2019 https://doi.org/10.1109/TMI.2019.2901928

[12] Reliability of tumor segmentation in glioblastoma: Impact on the robustness of MRI-radiomic features, Tixier F et al, Med Phys. 2019 August; 46(8):3582-3591. https://doi.org/10.1002/mp.13624

[13] Can computer-aided diagnosis assist in the identification of prostate cancer on prostate MRI? a multi-center, multi-reader investigation, Gaur S et al, Oncotarget, 2018, Vol. 9, (No. 73), pp: 33804-33817 https://doi.org/10.18632/oncotarget.26100

The invention claimed is:

1. A method of estimating an amount of at least one biomarker for a subject, based on an image of the subject imaged by a medical imaging method, the method comprising:
   processing the image to identify at least one tissue type within a region of interest of the image and determining an amount of each identified tissue type;
   associating each identified tissue type with a measure of biomarker production;
   calculating a total amount of biomarker production for the identified tissue types.

2. The method of claim 1, wherein at least one of the at least one tissue types is an abnormal tissue type.

3. The method of claim 2, wherein the abnormal tissue type is associated with the production of the at least one biomarker at a level higher by a predetermined amount, or lower by a predetermined amount, than a normal level associated with a normal tissue type, optionally wherein the abnormal tissue type is tumour tissue and/or cancer tissue.

4. The method of claim 1, wherein at least two tissue types are identified, optionally wherein at least one of the at least two tissue types is a normal tissue type, optionally wherein the normal tissue type is associated with the production of the at least one biomarker at a normal level, and optionally wherein the normal level is zero.

5. The method of claim 4, wherein the probability of a region the image corresponding to a particular tissue type is determined based on characteristics of the image data.

6. The method of claim 4, wherein the probability of a region the image corresponding to a particular tissue type is determined, at least in part, based on relevant clinical data about the subject.

7. The method of claim 6, wherein the relevant clinical data comprise one or more of: age, actual biomarker level, previous biomarker level, digital rectal examination result, indicator of known or suspected inflammation, indicator of known or suspected infection, family history of related cancer types, histopathology results obtained from tissues associated with suspected cancer, genetic tests associated with a suspected cancer, family history or ethnic group membership associated with increased or decreased risk of cancer or biomarker production.

8. The method of claim 1, wherein the processing of the image comprises identifying a most probable type of tissue present at a region of the image within the region of interest from a plurality of possible tissue types.

9. The method of claim 1, wherein the processing of the image comprises identifying a plurality of possible tissue types present at a region of the image within the region of interest and a respective probability of the region the image corresponding to each possible tissue type, and the calculation of total biomarker production includes weighting a measure of biomarker production associated with each possible tissue type by their respective probability.

10. The method of claim 1, wherein the identified tissue types are adjusted based on data input by a human.

11. The method of claim 1, wherein each identified tissue type is associated with a measure of biomarker production based on a database of biomarker production for possible tissue types.

12. The method of claim 1, wherein the measure of biomarker production associated with a tissue type is based, at least in part, on subject-specific characteristics, optionally wherein the characteristics include at least one of: a measure of the subject's tissue metabolism, a measure of the subject's heart rate.

13. The method of claim 1, wherein a plurality of different tissue types with relative probabilities are identified for a region of the image, and the total amount of biomarker production comprises an expected range within a predetermined confidence interval.

14. The method of claim 1, wherein the medical imaging method comprises one of: MRI, CT, PSMA PET CT, choline PET CT.

15. The method of claim 1, wherein the biomarker comprises one of: PSA, Immunoglobulin, CA 125, calcitonin, AFP, HCG, circulating tumour cells, circulating tumour DNA.

16. The method of claim 1, wherein the biomarker is PSA, the imaging method is MRI, and the region of interest comprises the subject's prostate.

17. The method of claim 1, further comprising determining a variance for biomarker production by means of one or more of the following:
   (i) associating a biomarker density variance with at least one tissue type
   (ii) determining a variance of a volume estimate of at least one tissue type
   (iii) determining a plurality of biomarker production levels corresponding to a different possible identified tissue types for a region of the image, different scenarios and/or different conditions.

18. A computer program product configured to perform the steps of the method according to claim 1, when executed on a computer.

19. A method of estimating biomarker production of a particular tissue type, the method comprising:
   processing images of a plurality of test subjects with known biomarker levels imaged with a medical imaging method to identify one or more tissue types within a region of interest;
   determining, by a machine learning method, a relationship between the amount of each tissue type and the known biomarker level;
   calculating an estimated biomarker production for a predetermined amount of each tissue type.

20. The method of claim 19, further comprising determining a variance for the estimated biomarker production, by:
   calculating an estimated total amount of biomarker for an image of a test subject based on the estimated biomarker production; and
   comparing the estimated total amount of biomarker with an actual amount of biomarker for the test subject.

* * * * *